United States Patent
Cohen

(10) Patent No.: US 10,384,003 B2
(45) Date of Patent: Aug. 20, 2019

(54) MASS VACCINATION DEVICE

(71) Applicant: SYRINJECTOR Ltd., Petach Tikva (IL)

(72) Inventor: Nahum Cohen, Karmey Yosef (IL)

(73) Assignee: SyrinJector Ltd, Gedera (IL)

( * ) Notice: Subject to any disclaimer, the term of this patent is extended or adjusted under 35 U.S.C. 154(b) by 359 days.

(21) Appl. No.: 14/417,167

(22) PCT Filed: Jul. 26, 2013

(86) PCT No.: PCT/IB2013/056133
§ 371 (c)(1),
(2) Date: Jan. 26, 2015

(87) PCT Pub. No.: WO2014/016807
PCT Pub. Date: Jan. 30, 2014

(65) Prior Publication Data
US 2015/0174321 A1    Jun. 25, 2015

Related U.S. Application Data

(60) Provisional application No. 61/675,894, filed on Jul. 26, 2012.

(51) Int. Cl.
*A61M 5/172* (2006.01)
*A61M 5/14* (2006.01)
(Continued)

(52) U.S. Cl.
CPC ............ *A61M 5/172* (2013.01); *A61D 1/025* (2013.01); *A61M 5/1407* (2013.01);
(Continued)

(58) Field of Classification Search
CPC ... A61D 1/025; A61M 5/1407; A61M 5/1408; A61M 5/16827; A61M 5/172; A61M 2005/1726; A61M 5/3294; A61M 5/3295; A61M 5/3298; A61M 2250/00; A61M 5/1409; A61M 5/1413; A61M 5/142; A61M 5/14244; A61M 5/168; A61M 5/16831;
(Continued)

(56) References Cited

U.S. PATENT DOCUMENTS 3,949,746 A    4/1976 Wallach
5,269,762 A    12/1993 Armbruster et al.
(Continued)

FOREIGN PATENT DOCUMENTS

CA    2354824          2/2003
CA    2354824 A1 *    2/2003    ............ A61D 1/025
(Continued)

OTHER PUBLICATIONS

International Search Report for corresponding PCT application PCT/IB2013/056133 dated Jan. 9, 2014.

*Primary Examiner* — Shefali D Patel
(74) *Attorney, Agent, or Firm* — Heidi Brun Associates Ltd.

(57) ABSTRACT

A system for mass vaccinations including an electronic injector device having at least one needle for administering a measured amount of a vaccine; and an electronic fluid delivery device to deliver variable vaccine dosages to the injector device, and to deliver the measured amount of the vaccine.

16 Claims, 6 Drawing Sheets

(51) Int. Cl.
*A61M 5/20* (2006.01)
*A61M 5/32* (2006.01)
*A61D 1/02* (2006.01)
*A61M 5/142* (2006.01)
*A61M 5/168* (2006.01)
*A61M 5/44* (2006.01)

(52) U.S. Cl.
CPC .... *A61M 5/14244* (2013.01); *A61M 5/16827* (2013.01); *A61M 5/1723* (2013.01); *A61M 5/20* (2013.01); *A61M 5/2066* (2013.01); *A61M 5/3294* (2013.01); *A61M 5/3295* (2013.01); *A61M 5/14216* (2013.01); *A61M 5/204* (2013.01); *A61M 5/445* (2013.01); *A61M 2005/1726* (2013.01); *A61M 2005/2013* (2013.01); *A61M 2005/2026* (2013.01); *A61M 2205/13* (2013.01); *A61M 2205/3324* (2013.01); *A61M 2205/3327* (2013.01); *A61M 2205/3576* (2013.01); *A61M 2250/00* (2013.01)

(58) Field of Classification Search
CPC .. A61M 5/16836; A61M 5/1723; A61M 5/20; A61M 5/204; A61M 5/2066; A61M 2005/2006; A61M 2005/2013; A61M 2005/2026; A61M 2205/13; A61M 2205/33; A61M 2205/3306; A61M 2205/3313; A61M 2205/3324; A61M 2205/3327; A61M 2205/3379; A61M 2205/3576; A61M 2205/50; A61M 2230/005

See application file for complete search history.

(56) References Cited

U.S. PATENT DOCUMENTS

| | | |
|---|---|---|
| 6,796,964 B2 * | 9/2004 | Eidson ............... A61D 7/00 604/135 |
| 6,858,020 B2 | 2/2005 | Rusnak |
| 7,488,309 B2 | 2/2009 | Kissinger et al. |
| 7,802,541 B2 | 9/2010 | Jones et al. |
| 7,850,665 B2 | 12/2010 | Johnston, Jr. et al. |
| 8,087,386 B2 | 1/2012 | Purswell et al. |
| 2006/0247578 A1 | 11/2006 | Arguedas et al. |
| 2011/0264033 A1 * | 10/2011 | Jensen ............... A61M 5/1452 604/65 |

FOREIGN PATENT DOCUMENTS

| | | | |
|---|---|---|---|
| WO | 2004101060 A2 | 11/2004 | |
| WO | WO 2004101060 A2 * | 11/2004 | ............ A61D 1/025 |
| WO | 2009085331 A1 | 7/2009 | |
| WO | WO 2009085331 A1 * | 7/2009 | ............ A61M 5/19 |
| WO | 2012008842 A1 | 1/2012 | |
| WO | WO 2012008842 A1 * | 1/2012 | ............ A61D 1/025 |

* cited by examiner

MASS VACCINATION DEVICE

This application is a national phase of PCT International Application Number PCT/IB2013/056133, filed on 26 Jul. 2013, published as WO 2014/016807, which in turn claims priority and benefit from U.S. Provisional Patent Application No. 61/675,894, filed on 26 Jul. 2012, both of which are hereby incorporated by reference in their entirety.

FIELD OF THE INVENTION

The present invention relates to mass vaccination devices generally and to an automatic mass vaccination device in particular.

BACKGROUND OF THE INVENTION

Vaccinations may be used to prevent and/or reduce the effects of diseases in living creatures. They may be administered in different stages of the life of a human or an animal, depending on the type of disease the vaccine is designed to prevent or treat. In poultry for example, some vaccines may be administered the first day a chick hatches, while others may be administered when the chicks are several weeks old, and in some cases when they are several months old.

Animal vaccination typically involves vaccinating many animals at a substantially same time. The animals may all be part of a same herd or flock, and may sometimes include animals from neighboring herds (or flocks), which may sometimes number into the hundreds and even the thousands. Mass vaccination devices are frequently used to perform these vaccinations, the majority of these devices generally configured for automatic or semi-automatic operation.

An example of a mass vaccination device is described in WO 2004/101060 A2, "AUTOMATIC INJECTOR FOR MASS INJECTIONS", which describes "an injection assembly adapted to be carried by a user for mass injection of a medical material. The assembly comprises dosing unit (100.1) adapted to push predetermined doses of the medical material, propelling means adapted to actuate the dosing unit, means for supplying the medical material, controller (200), and automatic injector (500) that comprises housing, movable needle that can be housed or protruded so as to discharge the medical material received from the housing unit. Contact sensor and positioning sensor delivers information to the controller (200) and the controller (200) orders the propelling means as well as the dosing unit (100.1) and the needle to automatically push the medical material. The assembly can be provided with means for supplying antiseptic material in order to disinfect the needle between injections and in case of injecting humans, the assembly comprises a needle magazine so as to change the needles. The apparatus can be provided with electronically or physical marker for recording".

Another example is described in U.S. Pat. No. 6,796,964 B2, "AUTOMATIC VETERINARY MEDICAMENT DELIVERY SYSTEM", which describes "an electrically powered, plunger-free, valve-free adjustable veterinary delivery system for the administration of veterinary pharmaceuticals or vaccines to a variety of poultry or livestock. The delivery system includes a rechargeable battery positioned to power an electric motor which is used to actuate a peristaltic pump that propels pre-determined quantity of fluid medicament through the system for delivery. The system teaches adjustable dosage control of the fluid medicament by means of an electronic control unit which uses photo-optic sensor to calibrate dosage. The veterinary delivery system includes several hand-held injection devices from which to choose, depending on desired use, each having a push-button trigger, at least one needle, a headlight, signal lights, optional dye marking means, and an optional mixing chamber for mixing medicaments at the time of delivery of the medicament, the hand-held injection devices being easily connected and disconnected by means of quick connect fluid couplers for being in fluid communication with the system and a nine-pin amp electrical connector for being in electronic communication with the control unit".

A third example of a mass vaccination device is described in U.S. Pat. No. 7,802,541, "POULTRY VACCINATION APPARATUS AND METHOD", which describes "an apparatus for providing multiple vaccinations of poultry simultaneously is described. A neck injection, breast injection, two wing injections, and an eye mist or drop may be performed in one operation. The apparatus holds the bird in position for precise location of injections, thereby reducing wasted vaccine. The risk of injury to the bird during the process is minimized by greatly reducing the manual handling of the bird during vaccination. Vaccination costs are also reduced by the reduction of labor otherwise required in this process".

Other examples of mass vaccination devices are described in U.S. Pat. Nos. 3,949,746; 6,858,020; US 2006/0247578 A1; and U.S. Pat. No. 5,269,762.

SUMMARY OF THE PRESENT INVENTION

There is provided, in accordance with an embodiment of the present invention, a system for mass vaccinations including an electronic injector device having at least one needle for administering a measured amount of a vaccine; and an electronic fluid delivery device adapted to deliver variable vaccine dosages to the injector device, and further adapted to deliver the measured amount of the vaccine.

In accordance with an embodiment of the present invention, the at least one needle is a poultry vaccination needle.

In accordance with an embodiment of the present invention, the injector device is a single hand handheld device.

In accordance with an embodiment of the present invention, the electronic fluid delivery device is a portable device.

In accordance with an embodiment of the present invention, the injector device additionally includes an interconnecting cable for fluidly communicating the injector device and the fluid delivery device.

In accordance with an embodiment of the present invention, the cable is a flexible cable.

In accordance with an embodiment of the present invention, the cable includes a fluid conductor for delivering the variable vaccine dosages and the measured amount of the vaccine.

In accordance with an embodiment of the present invention, the cable includes a power conductor for sharing electrical power between the injector device and the fluid delivery device.

In accordance with an embodiment of the present invention, the cable includes a data communication conductor for communicating between the injector device and the fluid delivery device.

In accordance with an embodiment of the present invention, the injector device includes a plurality of fluid mixing compartments for mixing the measured amount of the vaccine.

In accordance with an embodiment of the present invention, the injector device includes a means to distribute the measured amount of the vaccine among the plurality of fluid mixing compartments.

In accordance with an embodiment of the present invention, the injector device includes a sensor to measure at least one of a physical, mechanical, and chemical characteristic of the measured amount of the vaccine.

In accordance with an embodiment of the present invention, the sensor measures a wavelength of the measured amount of the vaccine.

In accordance with an embodiment of the present invention, the injector device includes a contact sensor to sense proximity to body tissue.

In accordance with an embodiment of the present invention, the contact sensor is a pressure sensor.

In accordance with an embodiment of the present invention, the injection fluid delivery device includes at least one temperature storage module for controlling a temperature of a vaccine container.

In accordance with an embodiment of the present invention, the vaccine container is a flexible bag.

In accordance with an embodiment of the present invention, the vaccine container is a bottle.

In accordance with an embodiment of the present invention, the injection fluid delivery device includes at least one variable-volume pump.

In accordance with an embodiment of the present invention, the injector device further comprises at least two needles.

There is provided, in accordance with an embodiment of the present invention, a method of mass vaccination using an automatic mass vaccination system, the method includes pressing a vaccination trigger on an injector device having at least one needle for administering a measured amount of a vaccine; automatically detecting contact between the electronic injector device and body tissue; and automatically delivering the measured amount of the vaccine to the injector device from a device adapted to deliver variable vaccine dosages.

In accordance with an embodiment of the present invention, the method includes automatically distributing the measured amount of a vaccine among a plurality of fluid mixing compartments.

In accordance with an embodiment of the present invention, the method includes mixing the measured amount of the vaccine in the fluid mixing compartments.

In accordance with an embodiment of the present invention, the method includes automatically measuring at least one of a physical, mechanical, and chemical characteristic of the measured amount of the vaccine.

In accordance with an embodiment of the present invention, the method includes automatically injecting into body tissue through the at least one needle the measured amount of the vaccine responsive to the measurement.

In accordance with an embodiment of the present invention, the method includes automatically applying a disinfectant to the at least one needle following the injecting.

There is provided, in accordance with an embodiment of the present invention, a method of simultaneously injecting a plurality of vaccine dosages into body tissue using an electronic syringe injector including a single needle, the method includes delivering the plurality of vaccine dosages to the electronic syringe injector through a plurality of conduits, wherein each vaccine dosage of the plurality of vaccine dosages is delivered over a separate conduit; and in the electronic syringe injector, conducting each received vaccine dosage of the plurality of vaccine dosages through a separate conduit connected to the one needle.

In accordance with an embodiment of the present invention, the body tissue is poultry body tissue.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
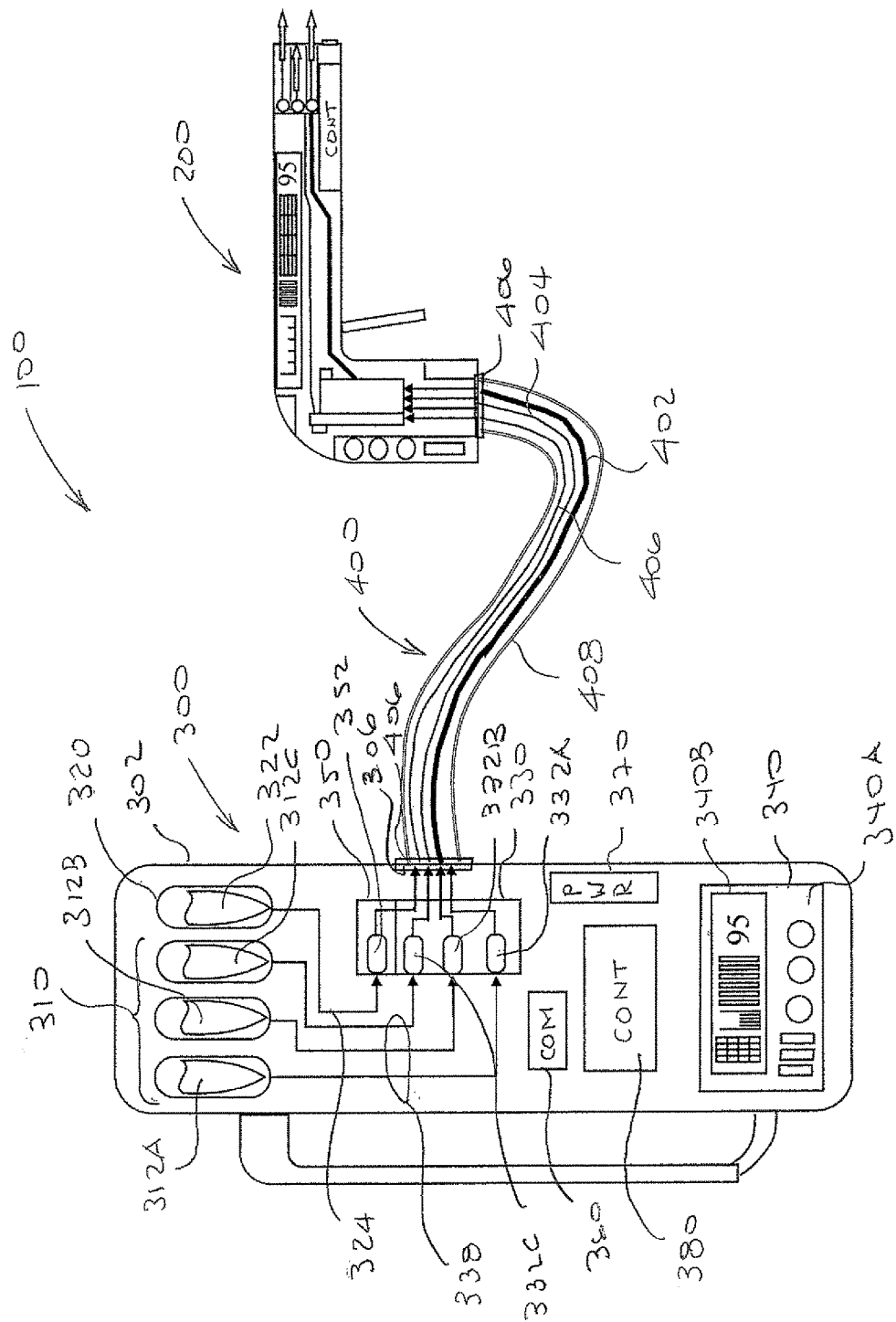
FIG. 1 schematically illustrates an automatic mass vaccination system (AMVS), according to an embodiment of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Applicants have realized that known techniques used in systems for mass vaccination of poultry and other animals require extensive manual operator (user) involvement. This may cause a mass vaccination operation to be slow and tedious, which may have serious negative consequences particularly when the operation is being carried out to prevent the outbreak or quick spreading of a disease. Additionally, stress may be induced in the animals, possibly affecting the efficacy of the treatment being provided (among other possible negative effects). Such is the case, for example, with mass vaccination systems using only one needle for injecting multiple dosages into an animal. With these systems, the animal must be injected several times which, aside from being a slow process, may additionally induce stress in the animal. Some mass vaccination systems attempt to overcome the problems of using a single needle by including multiple needles for injecting multiple dosages substantially at the same time. Generally, these systems use fixed-volume vaccine dispensers which may require frequent replacement of the vaccine dispensers in order to accommodate the dispenser size to the size of the animal.

Applicants have realized that known techniques used in mass vaccination systems may be combined with suitable automation means to arrive at a substantially improved automatic mass vaccination system allowing quick mass vaccinations. The automatic mass vaccination system may allow quick simultaneous injection delivery of multiple vaccines or drugs (hereinafter "vaccines") in varied dosages into any kind of live animal tissue including poultry tissue, and also into live human tissue. The automatic mass injection system may also be suitable for quick injection delivery of a single vaccine or drug (hereinafter "vaccine") into animal tissue and human tissue.

Applicants have further realized that automatically varying the sizes of dosages may allow different dosages of vaccines to be administered to different-sized animals in a herd (or poultry in a flock) without interrupting a user's progress during mass vaccinations. This may be potentially advantageous over known mass vaccination systems which may require components (e.g. vaccine dispenser) to be replaced to accommodate for variations in the sizes of the animals, and may as a result the user's progress Applicants have further realized that the automatic mass vaccination system may be implemented as a relatively light weight, fully portable system which may be singly transported by a user. The automatic mass vaccination system may include a handheld syringe injector for injecting the animals and an injection fluid delivery device housed inside a vaccine storage bag which may be worn by the user, thus allowing the user to quickly move among, and vaccinate, animals in a herd (or poultry in a flock).

Automatic Mass Vaccination System

Figure 2:
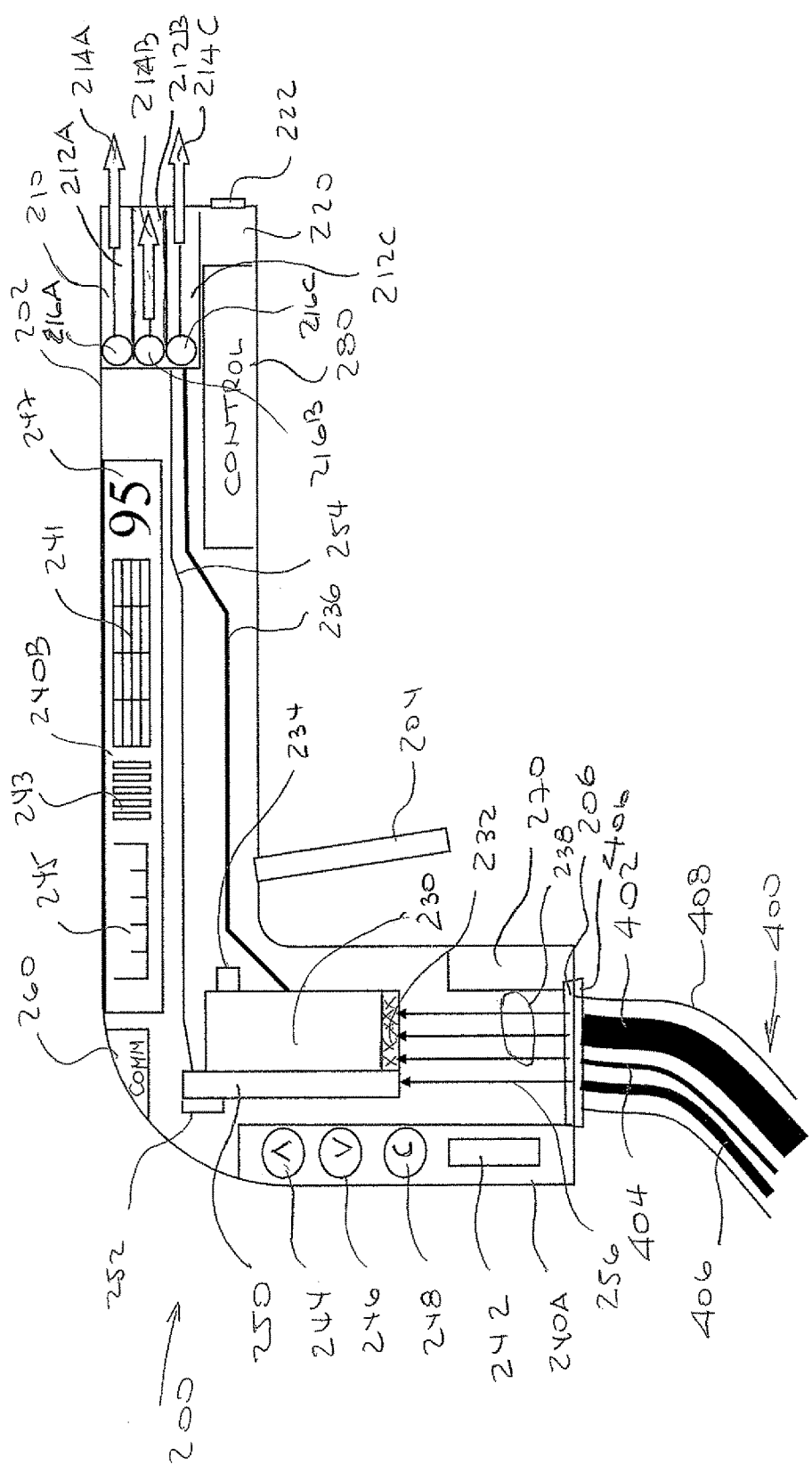
FIG. 2 schematically illustrates an enlarged view of a handheld syringe injector in the AMVS of FIG. 1, according to an embodiment of the present invention.

Reference is now made to FIG. 1 which schematically illustrates an automatic mass vaccination system (AMVS) 100, according to an embodiment of the present invention. AMVS 100 may include a handheld syringe injector 200, an injection fluid delivery device 300, and an interconnecting flexible cable 400 connecting the handheld syringe injector 200 to the injection fluid delivery device 300. Reference is also made to FIG. 2 which schematically illustrates an enlarged view of handheld syringe injector 200, according to an embodiment of the present invention.

Handheld Syringe Injector

Handheld syringe injector 200 may be an electrically operated, relatively lightweight syringe injector which may be held in a single hand by a user for individually injecting live animals, including poultry. Syringe injector 200 may be used for mass vaccination operations, and may also be used for vaccinating animals individually as part of an individual vaccination operation. When suitably fitted, syringe injector 200 may be used for vaccinating live humans. Syringe injector 200 may include a syringe drive module 210, a contact sensing module 220, a fluid mixing module 230, a user interface module 240 (240A and 240B), a disinfectant module 250, a communication module 260, and a power supply module 270.

Syringe injector 200 additionally includes a housing 202 for housing modules 210-280, which may be gun-shaped. Syringe housing 200 may include means to allow easy access to modules 210-280 which may be modularly replaceable, allowing a user to quickly replace a module in case of failure or when required. Syringe injector 200 may additionally include a trigger 204 for initiating a vaccination process when the trigger is pressed, as described further on below. Alternatively, syringe injector 200 may include any other suitable shape for comfortable fit and easy manipulation in the single hand of the user, as well as any other suitable activation means (for example, a button) for initiating the vaccination process. Syringe injector 210 may additionally include a connector 206 which may serve as an interface for connecting means for supplying fluids (vaccines, disinfectant), for conducting electric power, or for enabling data communications, or any combination thereof.

Syringe Injector—Syringe Drive Module

Syringe drive module 210 may accommodate one or more needles inside needle housings, for example 3 needle housings 212A, 212B, and 212C with needles 214A, 214B, and 214C as shown in FIG. 2. Syringe drive module 210 may include means, for example motors 216A, 216B and 216C, which may drive the needles pushing a portion of the length of needles 214A-214C out of needle housings 212A-212C and out of the syringe drive module causing the needles to protrude outwards from syringe injector 200. Motors 216A-216C may additionally retrieve needles 214A-214C back into needle housings 212A-212C in syringe drive module 210 so that the needles do not protrude from syringe injector 200.

Motors 216A-216C may drive the needles so that any combination of needles 214A-214B may be simultaneously pushed outwards from syringe drive module 210. For example, only one syringe may be pushed outwards to vaccinate an animal while the other two needles remain retracted in syringe drive module 210, or two needles may simultaneously be pushed outwards to vaccinate the animal while the third needle remains retracted, or three needles may simultaneously be pushed outwards to vaccinate the animal. Retraction of the protruding needles may also be simultaneously performed following vaccination of the animal.

Motors 216A-216C may push needles 214A-214C so that all protrude a same length from syringe drive unit 210, or one or more protrude a different length. Furthermore, motors 216A-216C may drive needles 214A-214C so that the protruding lengths of the needles may vary, for example, longer for one animal and shorter for another, depending on the type of animal (e.g. horse, cow, chicken, goose), the size of the animal (e,g, 1-day old chicken, full grown chicken), and other veterinary-related factors. As an example, the protruding length of the needles may be greater for vaccinating a full grown chicken compared to the length required to vaccinate a one day old chick, and may be even greater for vaccinating a cow.

Vaccine flow through needles 214A-214C may depend on whether the needles are protruding (e.g. needles 214A and 214C) or retracted (e.g. needle 214B). In the extended position, vaccine fluid may be delivered through needles 214A and 214C into the animal tissue. while in the retracted position, there is no vaccine fluid flow through needle 214C. In a non-vaccination mode, needles 214A-214C are retracted inside syringe drive module 210.

Needle housings 212A-212C may each be fitted with more than one needle, each of which may be used a predetermined number of times before being replaced by a new needle in the housing. For example, each needle housing 212A-212C may be fitted with 3 needles, 5 needles, 10 needles, 20 needles, 50 needles, or more. Syringe drive module 210 may include means which allow the needles to be readily replaced inside each needle housing 212A-212C once having been used the predetermined number of times, for example, using a controller-activated spring mechanism or other known technique, which may interact with motors 216A-216C for driving the needles. Once all needles in any one of needle housings 212A-214A have been used up, the needle housing may be replaced. Syringe drive module 10 may additionally include means to detect movement of each needle to count how many times a needle in a syringe is used, for example, by using mechanical sensing means, optical detection means, or other suitable known detection means capable of detecting movement of the needles.

Syringe Injector—Contact Sensing Module

Contact sensing module 220 may be part of a self-stabbing prevention mechanism which may prevent inadvertent activation of syringe driver module 210 and inadvertent driving of any one of needles 214A-214C out of the syringe driver module (as previously mentioned, in a non-vaccination mode, needles 214A-214C are retracted inside syringe driver module). Contact sensing module 220 may include a sensor 222 which may sense contact with animal tissue (and human tissue). Sensor 222 may be a pressure sensor, an electro-mechanical sensor, an optical sensor, an IR sensor, or any other type of suitable known contact or proximity sensor.

The self-stabbing prevention mechanism using contact sensing module 220 may operate in the following exemplary manner. In order for syringe driver module 210 to be activated, sensor 222 must sense contact with animal tissue and at least one other activation means in syringe injector 200 must be operated on by the user, for example, by pressing on trigger 204. If only there is sensing of contact with animal tissue but trigger 204 is not pressed, then syringe driver module 210 is not activated and needles 214A-214C remain in their retracted position. Additionally, if trigger 204 is pressed but sensor 222 does not detect contact with animal tissue, similarly syringe driver module 210 is not activated and needles 214A-214C remain retracted.

Syringe Injector—Fluid Mixing Module

Fluid mixing module 230 may include one or more fluid mixing compartments in fluid communication with the needles in syringe driving module 210 through vaccine lines 236. Each compartment is associated with a particular needle and may be filled with a predetermined vaccine dosage which is to be administered to an animal through its corresponding needle. The vaccine dosage may be a single vaccine or may include multiple vaccines which are mixed in the compartment. The number of compartments may be equal to the number of needles in syringe drive module 210, for example 3 compartments corresponding to needles 214A-214C.

Fluid mixing module 230 may additionally include a controller-operated vaccine mixer 232 to distribute the vaccines separately flowing through connector 206 into syringe injector 210 and into the fluid mixing compartments where they may be mixed according to the respective dosages. The vaccines separately flowing into syringe injector 210 may be transported to vaccine mixer 232 through vaccine conduits 238. The vaccines may be of a same type or of different types, and may include any number of vaccines, for example, 5 vaccines, 6 vaccines, 10 vaccines, 15 vaccines, 20 vaccines, or more, depending on the number of vaccine sources which may be connected to syringe injector 200. The vaccines may flow into syringe injector 200 from injection fluid delivery device 300, and may be through flexible cable 400. The distribution of the vaccines into the different mixing compartments may be based on information pre-programmed into system 100 or based on user input information prior to each vaccination. Fluid mixing module 230 may additionally include a vaccine quality detector 234 as part of a vaccine quality check mechanism to ensure that the quality of the dosage in each mixing compartment is satisfactory. If the quality is found to be unsatisfactory, the vaccine quality check mechanism may interrupt operation of the vaccination process, for example, by preventing the operation of motors 216A-216C so that needles 214A-2124 may not be driven. Vaccine quality detector 234, for example, may detect or measure characteristics associated with the dosage (in each mixing compartment and which may include physical, mechanical and/or chemical characteristics. For example, vaccine quality detector 234 may detect a color of the vaccine dosage (a single vaccine or multiple vaccines), or may measure specific gravity, density, or PH, among other possible characteristics which may be detected or measured and may be used to determine the quality of the vaccine dosage. Vaccine quality detector may detect, for example, the wavelength of light transmitted through the vaccine dosage which may then be compared to predetermined values to determine if the dosage is correct. Vaccine quality detector 234 may also detect a level of the vaccine in each compartment to verify that there is the correct amount.

Exemplary Operation of Fluid Mixing Module

As previously described, the mixing module may receive any number of vaccines from one or more vaccine sources and may distribute the vaccines to the mixing compartments where they may be mixed if required, and from there transported to the needles for injection into animal. For example, syringe injector 200 may include 3 needles 214A-214C, each needle in communication with a fluid mixing compartment in fluid mixing module 230 so that there are 3 fluid mixing compartments. As part of the example, assume that there are six different vaccine sources 1-6 and that it has been predetermined that the vaccine from source 1 is to be injected through needle 214A; the vaccines from sources 2, 3, and 5 are to be mixed and injected through needle 214B; and the vaccines from sources 4 and 6 are to be injected through needle 214C. The operation may be as follows: the vaccines flow to vaccine mixer 232 through separate vaccine conduits 238 and reach the controller-operated vaccine mixer. The vaccine mixer routes the vaccine from source 1 to a first mixing compartment connected to needle 314A from where it flows through a first vaccine line 236 and out the needle into the animal. The vaccine mixer routes the vaccines from sources 2, 3 and 5 to a second mixing compartment connected to needle 314B where they mix and flow through a second vaccine line 236 and out the needle into the animal. The vaccine mixer routes the vaccines from sources 4 and 6 to a third mixing compartment connected to needle 314C where they mix and flow through a third vaccine line 236 and out the needle into the animal.

Syringe Injector—Disinfectant Module

Disinfectant module 250 may include a fluid holding compartment for holding a disinfectant which may be used before and/or after every vaccination to disinfect needles 214A-214C. Disinfectant module 250 may additionally include an application means for applying the disinfectant to the needles, and which may include one or more spray nozzles for spraying the disinfectant onto the needles. The disinfectant application means may be located in syringe drive module 210 in close proximity to needles 214A-214C, and may receive the disinfectant fluid through disinfectant line 254. Additionally or alternatively, the application means may include a contact surface which includes the disinfectant and through which needles 214A-214C pass and their outer surface, or may use any other known technique which may be used to disinfect the needle and suitable for being accommodated inside of the syringe injector 200. The disinfectant may flow into syringe injector 200 from injection fluid delivery device 300, and may be through flexible cable 400. Additionally or alternatively, the disinfectant may be supplied from other sources which may be connected to syringe injector 210 through connector 206. A disinfectant transport conduit 256 may transport the disinfectant inside syringe injector 210 from connector 206 to the fluid holding compartment in disinfectant module 250.

Disinfectant module 250 may additionally include a disinfectant detector 252 which may be part of a disinfectant check mechanism to ensure that the needles are being disinfected. If the needles are not being disinfected, the disinfectant check mechanism may interrupt operation of the vaccination process, for example, by preventing the operation of motors 216A-216C so that needles 214A-214C may not be driven. Disinfectant detector 252 may additionally detect low levels of disinfectant in the fluid holding compartment, and that the disinfectant is not being adequately applied to needles 214A-214C before and/or after each vaccination.

Syringe Injector—Communication Module

Communication module 260 may be used for transferring data between syringe injector 200 and injection fluid delivery device 300 and may include a transmitter and a receiver, or a transceiver. The communication may be over wired means, for example through flexible cable 400 connecting syringe injector 200 and fluid delivery device 300. Additionally or alternatively, communication between syringe injector 200 and fluid delivery device 300 may be over wireless means and may include use of a Wi-Fi communications network, a personal area network (e.g. Bluetooth, ZigBee), a cellular phone network, among other suitable communication networks. Communication module 260 may also be used for downloading and uploading data to one or more remote communication devices over wired and/or wireless means, and may include uploading and downloading data over the Internet. The communication devices may include a smart phone, a personal computer, a tablet computer, a lap top computer, a remote server, or any other suitable computing device with communication and data transfer capability.

Syringe Injector—Power Supply Module

Power supply module 270 may be a DC voltage supply source and may supply DC voltage to modules 210-280. Power supply module 270 may include one or more replaceable batteries. Alternatively, power supply module may include rechargeable batteries and means to recharge the batteries by connecting the power supply module to an AC power line. The connection to the AC power line may be through an external AC/DC converter to which power supply module 270 may be connected. Additionally or alternatively, power supply module 270 may be connected to any DC power supply source suitable for recharging the batteries through a USB connection. For example, by connecting to a USB port in a PC or laptop computer, or to a smartphone/mobile charger, among other suitable DC supply sources. Power supply module 270 may alternately be powered by injection fluid delivery device 300 through flexible cable 400, and may include means only for distributing the DC power obtained from the fluid delivery device to modules 210-280. Additionally or alternatively, power supply module 270 may be used to supply DC power to fluid delivery device 300 over flexible cable 400.

Syringe Injector—User Interface Module

User interface module 240 may include a user control panel 240A to allow the user of AMVS 100 to enter data used to automatically operate the AMVS and to control activation of syringe injector 200. For example, user control panel 240A may include a power button 242 to turn the power on and off in syringe injector 200 (and may also turn power on and off in fluid delivery device 300 together with the syringe injector) and buttons for data entry 244-248. For example, the data entry buttons may be used for selecting from a menu-driven display using button 244 to move upwards in the menu, down button 246 to move downwards, and button 248 to clear the menu or a selection. User control panel 240A may additionally allow controlling activation of injection fluid delivery device 300 including data entry to the device.

User interface module 240 may additionally include display means 240B to display to the user the data entered and other data associated with the operation of AMVS 100. For example, display means 240B may include a power status (battery) indicator 243, an operational status indicator 245, and a digital display 247. Display means 240B may additionally include a touch screen 241 which may additionally or alternately be used for data entry. Display means 240B may additionally allow displaying data entered to injection fluid delivery device 300. A description of examples of types of data which may be entered and which may be displayed will be explained below with reference to injector control module 280 and FIG. 3.

Syringe Injector—Injector Control Module

Figure 3:
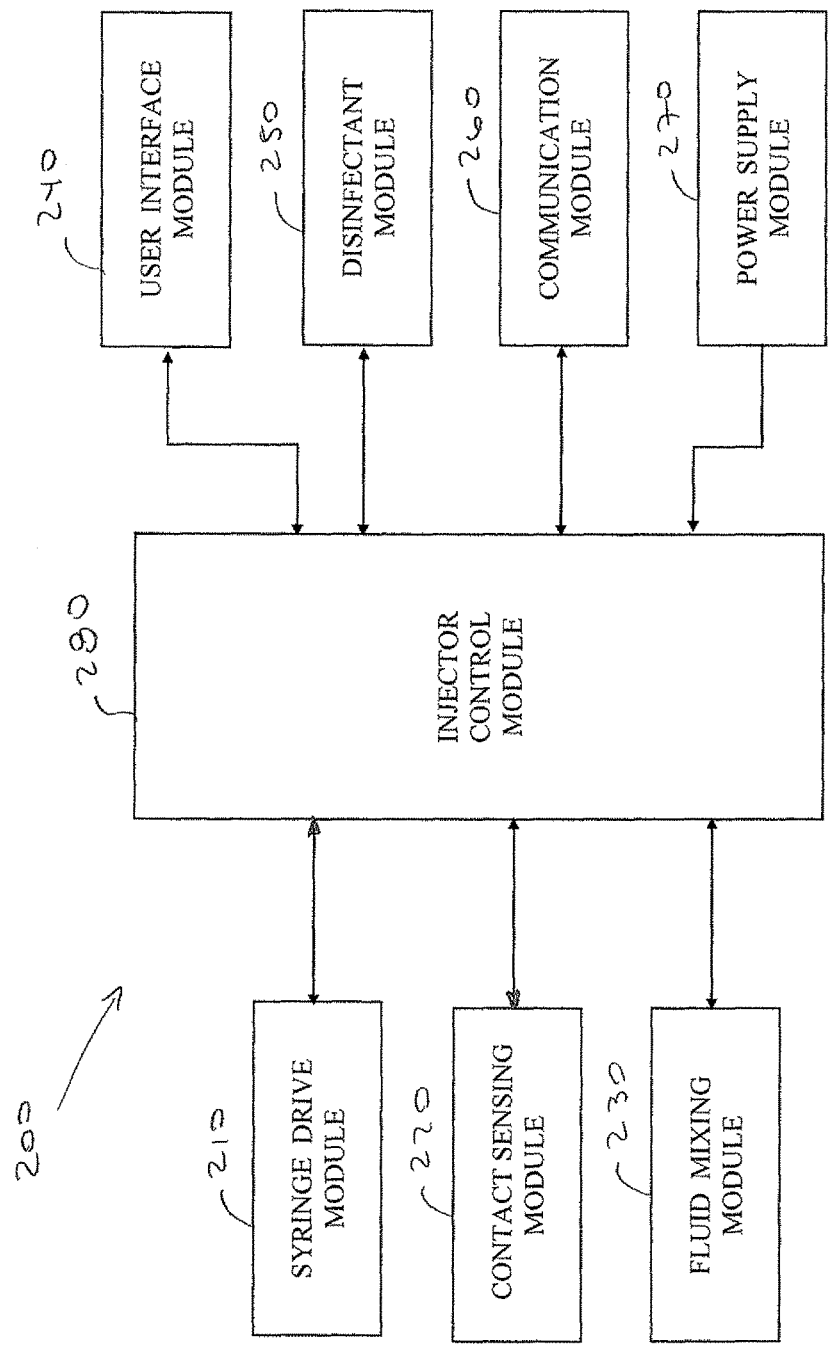
FIG. 3 schematically illustrates a functional block diagram illustrating the interfacing between injector control module 280 and the other modules in the syringe injector, according to an embodiment of the present invention.

Injector control module 280 may control the automatic operation of syringe injector 200, including the operation of modules 210-270 and activation of components therein. For example, injector control module 280 may check the operational status of all the modules, may activate and deactivate operation of components therein responsive to input data received, may communicate back and forth with remote devices, among other functions which may typically by carried out by a controller in processor-based devices. Reference is now also made to FIG. 3 which schematically illustrates a functional block diagram illustrating the interfacing between injector control module 280 and modules 210-270, according to an embodiment of the present invention.

Injector control module 280 may interface with syringe drive module 210 to individually operate motors 216A-216C for controlling which needles 214A-214C are used during each vaccination, and to control synchronization of needle movement to allow substantially simultaneous delivery of the vaccines through the needles. Injection control module 280 may additionally control the operation of motors 216A-216C to adjust the protrusion length of the needles for vaccination.

Injector control module 280 may interface with fluid mixing module 230 and may additionally control mixing of the vaccine dosages which flow from the fluid mixing module through vaccine lines 236 to syringes 212A-212C. Injector control module 280 operation of motors 216A-216C and of needles 214A-214C may be responsive to a user pressing trigger 204 and to signaling received from detector 222 in contact sensing module 220, from vaccine quality detector 234 in fluid mixing module 230, and from disinfectant detector 252 in disinfectant module 250, indicative that vaccination may be performed. Injector control module 280 receiving a signal associated with a condition where vaccination may not be performed (i.e. a warning signal is received from any one of the detectors) may prompt the injector control module to operate motors 261A-216C to retract all needles (or maintain retracted) and to issue a warning signal which may activate visual and/or audible warning alert means on syringe injector 200 and possibly also on injection fluid delivery device 300.

Injection control module 280 may control the operation of vaccine mixer 232 in fluid mixing module 230 to direct vaccines flowing through vaccine conduits 238 to the fluid mixing compartments. In the fluid mixing compartments, multiple vaccines flowing into a same compartment may be mixed. Information associated with the fluid mixing compartment where each vaccine is directed may be previously stored in injection control module 280. Additionally, information associated with which needle will receive which vaccine from which fluid mixing compartment may also be previously stored in injection control module 280. The previously stored information may be entered by a user through user interface module 240, and/or downloaded from a remote device through communication module 260. The previously stored data may additionally or alternately be downloaded from injection fluid delivery device 300. Alternatively, injection control module 280 may process data entered by a user through user interface module 240, and/or downloaded from a remote device through communication module 260, and may compute using a preprogrammed algorithm to which fluid mixing compartments the vaccines are directed and which syringe will be used. The processed information may be stored by injection control module 280.

Injection control module 280 may process data entered through user interface module 240 or downloaded through communication module 260 and may display the entered data and the processed data on display means 240B. Additionally the data entered through user interface module 240 and/or the processed data may be uploaded through communication module 260 to the remote device. Injection control module 280, through communication module 260, may share all or part of the entered data and/or the processed data with injection fluid delivery device 300.

Some examples of data which may be entered or downloaded from a remote device may include a number of needles in each syringe 212A-212C, maximum number of allowed vaccinations per needle, length of needle to be used in the next one or more vaccinations, number of dosages to be administered per needle, number of vaccine containers, types of vaccines in the vaccine containers, dosage amount per vaccine container, among other information which may be considered relevant to a mass vaccination operation. Some examples of data which may be displayed and/or uploaded to a remote computing device may include amount of dosages remaining in the vaccine containers, amount of vaccinations carried out, statistical information associated with the vaccination operation, date/start/finish time of vaccination, syringe used for vaccination, vaccines and dosages administered, user name and other applicable personal details, other details which may be relevant for tracking a mass vaccination operation.

Injection Fluid Delivery Device

Returning to FIG. 1, injection fluid delivery device 300 may be an electrically operated vaccine pumping device configured to be connected to syringe injector 200 and to supply measured amounts (dosages) of one or more vaccines to the syringe injector. The measured amounts of the one or more vaccines, which may include for example, 2 vaccines, 3 vaccines, 5 vaccines, 10 vaccines, or more, may be adjusted according to the vaccination requirements for each animal being vaccinated, and may include varying the mix of vaccines applied and/or the size of the dosages of the vaccines. Fluid delivery device 300 may supply the measured amounts of the one or more vaccines, for example 3 vaccines as shown in the figure by vaccine containers 312A, 312B, and 312C, through flexible cable 400 and through vaccine conduits 238 to the fluid mixing compartments in fluid mixing module 230.

Injection fluid delivery device 300 may include a temperature storage module 310, a disinfectant storage module 320, a vaccine delivery module 330, a user interface module 340, a disinfectant delivery module 350, a communication module 360, a power supply module 370, and a fluid delivery control module 380. Injection fluid delivery device 300 may be housed in a portable bag 302 configured to accommodate modules 300-380 including vaccine containers 312A-312C and a disinfectant container 322, and may additionally accommodate spare vaccine and disinfectant containers. Portable bag 302 may be a back pack, a front pack, or a side pack, or any combination thereof. Additionally or alternatively, portable bag 302 may be transported on a wheeled cart which may be pulled or pushed by a user, or may alternatively be motorized. A connector 306 may serve as an interface for connecting injection fluid delivery device 300 to flexible cable 400, which may allow establishing a fluid connection, a power connection, or a data communication connection, or any combination thereof, between the fluid delivery device and syringe injector 200.

Fluid Delivery Device—Temperature Storage Modules

Temperature storage modules 310 may accommodate in its interior vaccine containers 312A-312C, which may be relatively flexible vaccine bags or substantially rigid vaccine bottles, and may maintain the vaccines under controlled temperature conditions. Temperature storage modules 310 may include heating elements which may heat the interior of the temperature storage modules and which may allow each type of vaccine to be maintained at its recommended storage temperature. The recommended storage temperature may be the same or different for each vaccine container, for example vaccine bag 312A may be stored at a first temperature, vaccine bag 312B at a second temperature, and vaccine bag 312C at a third temperature.

Fluid Delivery Device—Disinfectant Storage Module

Disinfectant storage module 320 may accommodate in its interior one or more disinfectant containers 322 which may be used to disinfect needles 214A-214C in syringe injector 200, and which may additionally be used to disinfect all vaccine flow paths in AMVS 100 from storage temperature modules 310 to syringes 212A-212C. Disinfectant storage module may be similar to temperature storage module 10 but configured to accommodate the disinfectant container so that interior heating may not be required.

Fluid Delivery Device—Vaccine Delivery Module

Vaccine delivery module 330 may include a variable volume pumping mechanism which may allow pumping variable amounts of a vaccine dosage from each vaccine container 312A-312C to syringe injector 200. Vaccine delivery module 330 may include a variable volume pump for each vaccine container, for example a variable volume pump 332A which is fluidly connected to vaccine container 312A from which it receives the vaccine, a variable volume pump 332B which is fluidly connected to vaccine container 312B from which it receives the vaccine, and a variable volume pump 332C which is fluidly connected to vaccine container 312C from which it receives the vaccine. The fluid connection between pumps 332A-332C to vaccine containers 312A-312C may be through vaccine delivery conduits 338.

Variable volume pumps 332A-332C may each include a motor-driven piston inside a cylinder which may be moved forward or backwards to reduce or increase a fluid holding volume inside each cylinder. Each pump 332A-332C may be individually operated so that the vaccine dosage supplied by one pump may be different from that of the other pumps. Depending on the number of vaccines used, one or more of the pumps may not be operated. For example, if only the vaccines in vaccine containers 312A and 312C are required for the vaccination, then only pumps 332A and 332C are operated and 332B is left idle (or deactivated). A skilled person may realize that variable volume pumps 332A-332C may be implemented in other ways which may not necessarily be limited to a motor-driven piston inside a cylinder as previously described.

Fluid Delivery Device—User Interface Module

User interface module 340 may include a user control panel 340A to allow the user of AMVS 100 to enter data used to automatically operate the AMVS and to control activation of fluid delivery device 300. User control panel 340A may additionally allow controlling activation of syringe injector 200 including data entry to the device. User interface module 340 may additionally include display means 340B to display to the user the data entered and other data associated with the operation of AMVS 100. Display means 340B may additionally allow displaying data entered to syringe injector 200. User interface module 340 may be functionally similar to user interface module 240 in syringe injector 200, and the information entered, downloaded, or processed through either one of the devices (200, 300) may be equally displayed on the user interface modules of the other device.

Fluid Delivery Device—Disinfectant Delivery Module

Disinfectant delivery module 350 may include a pump 352 which is fluidly connected to disinfectant container 322 and from which it receives the disinfectant. The fluid connection between pump 352 to disinfectant container 322 may be through disinfectant delivery conduit 324. Pump 352 may be any suitable DC voltage electrically powered pump suitable for pumping disinfectant through flexible cable 400 and through disinfectant transport conduit 256 into disinfectant module 250 in syringe injector 200.

Fluid Delivery Device—Communication Module

Communication module 360 may be used for transferring data between injection fluid delivery device 300 and syringe injector 200 and may include a transmitter and a receiver, or a transceiver. Communication module 360 may also be used for downloading and uploading data to one or more remote communication devices over wired and/or wireless means, and may include uploading and downloading data over the Internet. Communication module 360 may be functionally similar to communication module 260 in syringe injector 200.

Fluid Delivery Device—Power Supply Module

Power supply module 370 may be a DC voltage supply source functionally similar to power supply module 270 in syringe injector 200, and may supply DC voltage to modules 310-380. Power supply module 370 may alternately be powered by syringe injector 200 through flexible cable 400, and may include means only for distributing the DC power obtained from the syringe injector to modules 310-380. Additionally or alternatively, power supply module 370 may be used to supply DC power to syringe injector 200 over flexible cable 400.

Fluid Delivery Device—Fluid Delivery Control Module

Figure 4:
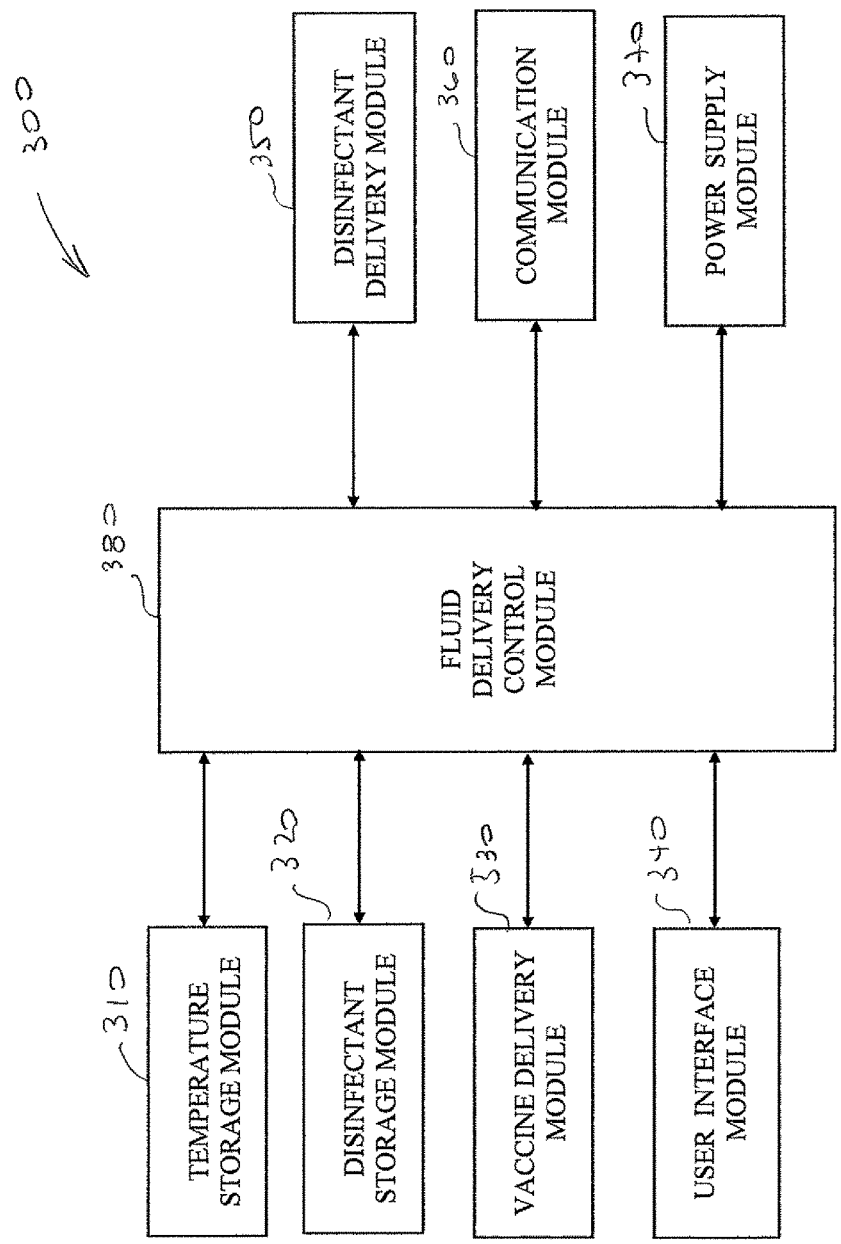
FIG. 4 schematically illustrates a functional block diagram illustrating the interfacing between the fluid delivery control module and the other modules in the injection fluid delivery device, according to an embodiment of the present invention.

Fluid delivery control module 380 may control the automatic operation of injection fluid delivery device 300, including the operation of modules 310-370 and activation of components therein. For example, fluid delivery control module 380 may check the operational status of all the modules, may activate and deactivate operation of components therein responsive to input data received, may communicate back and forth with remote devices, among other functions which may typically be carried out by a controller in processor-based devices. Fluid delivery control module 380 may also control operation of modules 310-370 responsive to data received from injector control module 280 in syringe injector 200. Reference is now also made to FIG. 4 which schematically illustrates a functional block diagram illustrating the interfacing between fluid delivery control module 380 and modules 310-370, according to an embodiment of the present invention. Fluid delivery control module 380 may additionally activate a warning signal which may be visually or audibly transmitted to the user, for example through user interface 240 in syringe injector 200 or user interface 340 in fluid delivery device 300, and which may be associated with detection of low levels of vaccines in vaccine containers 312A-312C, or of disinfectant in disinfectant container 322, or of failure in one of the components of modules 310-370, or low battery power conditions, among other conditions which may require user alert.

Fluid delivery control module 380 may interface with vaccine delivery module 330 to individually operate variable volume pumps 332A-332C for controlling an amount of vaccine to be pumped by each pump to syringe injector 200. Fluid delivery control module 380 may activate the pumps responsive to data received from injector control module 280 indicative that the fluid holding compartments in fluid mixing module 230 in syringe injector 200 may receive one or more new dosages of vaccines. Fluid delivery control module 380 may additionally control the volume in variable volume pumps 332A-332C based on information input to injection fluid delivery device 300 entered through user interface module 340, or downloaded to the fluid delivery device through communications module 360, or information communicated by injector control module 280 in syringe injector 200.

Fluid delivery control module 380 may interface with disinfectant delivery module 350 to operate pump 352 for supplying disinfectant to the fluid holding compartment in disinfectant module 250 in syringe injector 200. Fluid delivery control module 380 may activate pump 352 responsive to data received from injector control module 280 indicative that the level of disinfectant in disinfectant module 260 may be low. Fluid delivery control module 380 may automatically operate pump 352 every time one or more of variable volume pumps 332A-332C may be activated, or following a predetermined number of operations.

Fluid delivery control module 380 may process data entered through user interface module 340 or downloaded through communication module 360 and may display the entered data and the processed data on display means 340B. Additionally the data entered through user interface module 340 and/or the processed data may be uploaded through communication module 360 to the remote device. Fluid delivery control module 380, through communication module 360, may share all or part of the entered data and/or the processed data with syringe injector 200. Data which may be entered or downloaded from a remote device may be similar to that in syringe injector 200. Data which may be displayed and/or uploaded to a remote computing device may be similar to that in syringe injector 200.

Interconnecting Flexible Cable

Again referring back to FIG. 1, flexible cable 400 may serve to connect injection fluid delivery device 300 with syringe injector 200. Flexible cable 400 may include an exterior protective jacket 408 which may enclose any one of a fluid conductor 402, a power conductor 404, and a data communications conductor 408. Fluid conductor 402 may include one or more fluid conduits which may serve to connect a variable volume pump in vaccine delivery module 330 with a vaccine conduit 238 in syringe injector 200 and may allow vaccine fluid flow from the fluid delivery device to the syringe injector. Fluid conductor 402 may additionally connect pump 352 in disinfectant delivery module 350 with disinfectant module 250 in syringe injector 200. Power conductor 404 may connect power module 370 in fluid delivery device 300 with power supply module 270 in syringe injector 200 and may allow for DC power to be shared between the two devices. Data communications conductor 406 may connect communications module 360 in fluid delivery device 300 with communications module 260 in syringe injector 200, allowing data communications between the devices. Flexible cable 400 may include at each end a connector 406, which may be plug-and-play connectors, which connect with connector 306 in fluid delivery device 300 and with connector 206 in syringe injector 200. Flexible cable 400 may be reversible so that any one of the connectors at either end may connect with connector 206 and connector 306.

Exemplary Vaccination Operation

Figure 5:
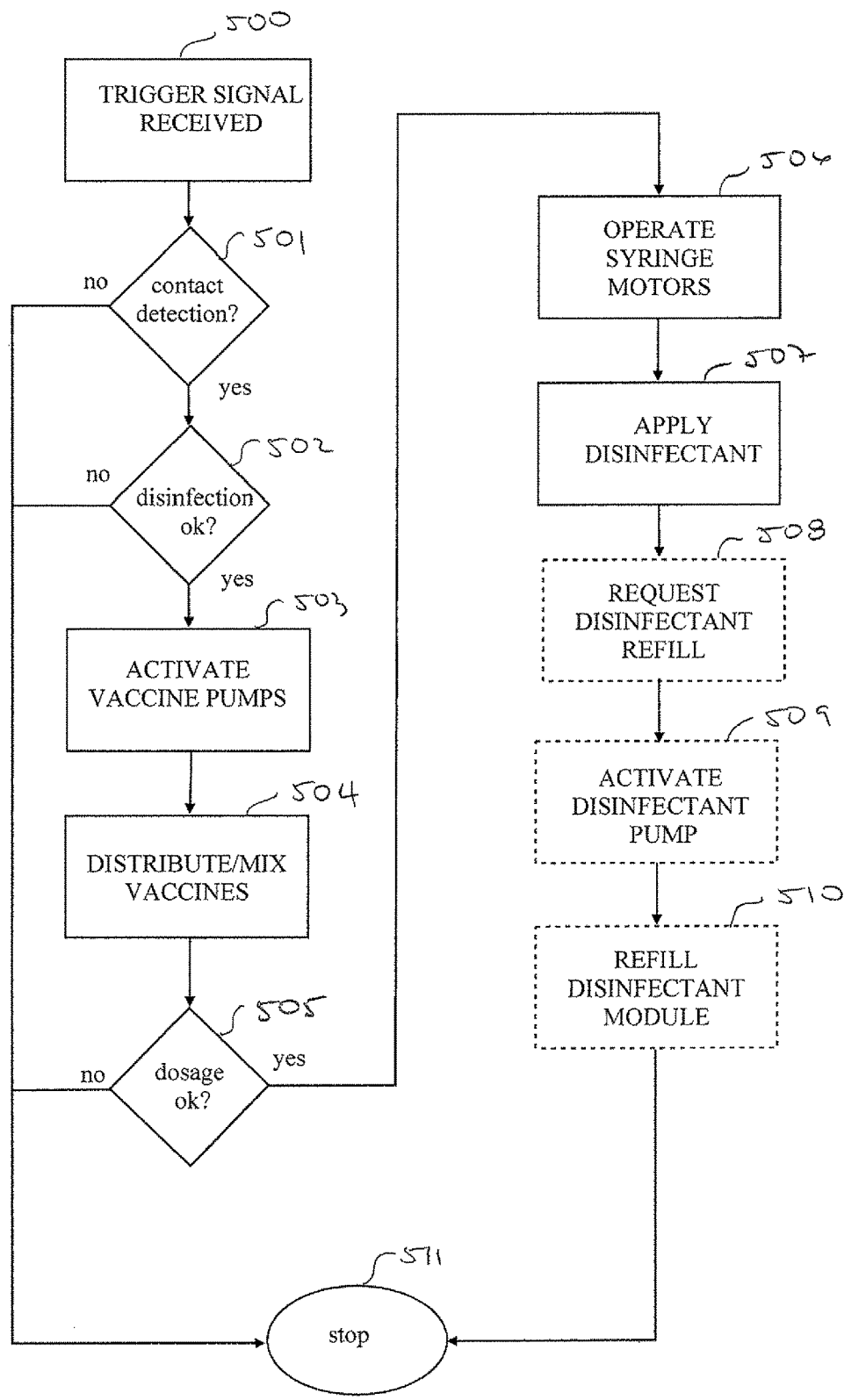
FIG. 5 is a flowchart of an exemplary method of operation of the AMVS, according to an embodiment of the present invention.

Reference is now made to FIG. 5 which is a flowchart of an exemplary vaccination operation of AMVS 100, according to an embodiment of the present invention. The method is described for illustrative purposes, and the skilled person may realize that the method may be practiced using more or less steps, or using a different sequence of the steps. For clarity purposes, the method is described with reference to AMVS 100.

At 500, injector control module 280 in syringe injector may receive a trigger signal associated with a user pressing trigger 204 in the syringe injector.

At 501, injector control module 280 may check that a detection signal received from contact sensing module 220 is indicative of sensor 222 detecting contact with animal tissue. If yes, continue to 502. If no, injector control module 280 may control operation of motors 216A-216C to retract needles 214A-214C into syringe drive module 210 and/or to maintain the needles retracted in the syringe drive module. Continue to 511.

At 502, injector control module 280 may check that a disinfection signal received from disinfection module 250 is indicative of sensor 253 detecting proper disinfection of needles 214A-214C and/or sufficient levels of disinfectant in the disinfection module. If yes, continue to 503. If no, injector control module 280 may control operation of motors 216A-216C to retract needles 214A-214C into syringe drive module 210 and/or to maintain the needles retracted in the syringe drive module. Continue to 511.

At 503, fluid delivery control module 380 may activate one or more of variable volume pumps 332A-332C in vaccine delivery module 330 and may pump vaccines through flexible cable 400 to syringe injector 200. The vaccines and the amounts of the dosages pumped may be according to data communicated from injector control module 280. Additionally or alternatively, the data may be entered into fluid delivery device 300 by the user through user interface module 340 or downloaded to the fluid delivery device through communication module 360.

At 504, injector control module 280 may control the operation of vaccine mixer 232 to distribute the vaccines to the fluid mixing compartments in fluid mixing module 230.

At 505, injector control module 280 may check that a vaccine quality check signal received from fluid mixing module 230 is indicative of sensor 234 detecting the correct characteristics in the dosages in the fluid mixing compartments in the fluid mixing module. If yes, continue to 506. If no, injector control module 280 may control operation of motors 216A-216C to retract needles 214A-214C into syringe drive module 210 and/or to maintain the needles retracted in the syringe drive module. Continue to 511.

At 506, injector control module 280 may operate one or more of motors 216A-216C for injecting vaccines through one or more of needles 214A-214C to an animal. Operation of the motors is according to data entered into syringe injector 200 by a user through user interface module 240 or downloaded to the syringe injector through communication module 260. One or more of needles 214A-214C may be pushed out of syringe drive module 210 for the vaccination and retracted following the injection.

At 507, injector control module 280 may send a command to disinfectant module 250 to apply disinfectant to needles 214A-214C following the injection and the needles are in the process of being retracted or have been retracted. If disinfection refill not required, continue to 511, otherwise continue to 508.

At 508, injector control module 280 may communicate with fluid delivery control module 380 in injection fluid delivery device 300 and may request supply of disinfectant to refill the fluid holding compartments in disinfectant module. This step may not need to be performed every time and may be performed periodically according to predetermined criteria, or upon user request, or upon injector control module 280 receiving a low level signal from disinfection module 250.

At 509, fluid delivery control module 380 may activate the pump in disinfectant delivery module 350 to pump disinfectant through flexible cable 400 to syringe injector 200.

At 510, injector control module 280 receives signal from disinfectant delivery module 350 that the fluid holding compartment is refilled. Injector control module 280 may communicate this information to fluid delivery control module 380.

At 511, injector control module 280 stops vaccination activities. If steps 500-510 were successfully completed injector control module 280 may enter a data acquisition/processing mode pending detection of a next trigger signal. If steps 500-510 were not successfully completed, injector control module 280 may maintain syringe injector 200 in an idle state pending corrective action by the user.

Figure 6:
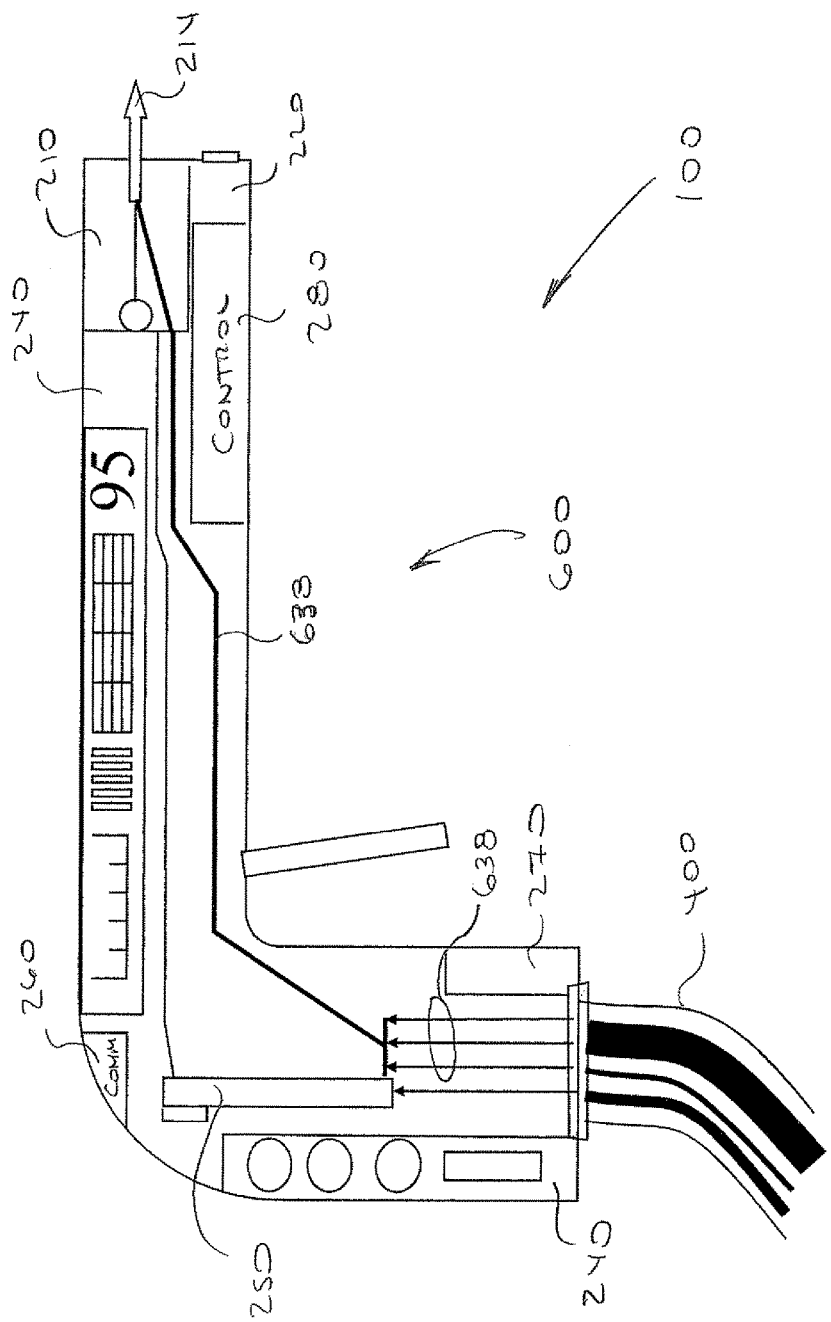
FIG. 6 schematically illustrates an exemplary single needle syringe injector for simultaneously delivering multiple vaccine dosages, according to an embodiment of the present invention.

Reference is now made to FIG. 6 which schematically illustrates an exemplary syringe injector 600 for use in AMVS 100, according to an embodiment of the present invention. Syringe injector 600 is a single needle electronic syringe injector configured to simultaneously deliver multiple vaccine dosages through a single needle 214. Syringe injector 600 may include modules 210, 220, 240, 250, 260, 270 and 280 similarly to syringe injector 200. Syringe injector 600 may receive the multiple vaccine doses from injection delivery device 300 through flexible cable 400 and may substantially simultaneously transfer the received vaccine doses, each dosage through an individual conduit 638 directly to a single needle 214 (each vaccine dose travels along its own conduit to the needle). Each conduit 638 may be connected to needle 214 at the luer end of the needle. The doses may be injected together through needle 214 into the animal where the vaccine doses may interact with one another and mix.

Unless specifically stated otherwise, as apparent from the preceding discussions, it is appreciated that, throughout the specification, discussions utilizing terms such as "processing," "computing," "calculating," "determining," or the like, refer to the action and/or processes of a computer, computing system, or similar electronic computing device that manipulates and/or transforms data represented as physical, such as electronic, quantities within the computing system's registers and/or memories into other data similarly represented as physical quantities within the computing system's memories, registers or other such information storage, transmission or display devices.

Embodiments of the present invention may include apparatus for performing the operations herein. This apparatus may be specially constructed for the desired purposes, or it may comprise a general-purpose computer selectively activated or reconfigured by a computer program stored in the computer. Such a computer program may be stored in a computer readable storage medium, such as, but not limited to, any type of disk, including floppy disks, optical disks, magnetic-optical disks, read-only memories (ROMs), compact disc read-only memories (CD-ROMs), random access memories (RAMs), electrically programmable read-only memories (EPROMs), electrically erasable and programmable read only memories (EEPROMs), magnetic or optical cards, Flash memory, or any other type of media suitable for storing electronic instructions and capable of being coupled to a computer system bus.

The processes and displays presented herein are not inherently related to any particular computer or other apparatus. Various general-purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the invention as described herein.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A portable system for mass vaccinations comprising:
   an electronic injector device comprising at least two needles for simultaneous injection delivery of a measured amount of multiple vaccines of different types in varied dosages to a body tissue;
   an electronic fluid delivery device comprising at least one variable-volume pump, adapted to quickly deliver said varied dosages of said multiple vaccines of different types to each of said at least two needles, and further adapted to deliver said measured amount of said multiple vaccines of different types;
   a vaccine quality detector to measure at least one of: a wavelength, a specific gravity, a density and a pH, to generate at least one measurement and to determine a quality of said measured amount of said multiple vaccines of different types according to said at least one measurement;
   a syringe driver module to accommodate said at least two needles;
   a contact sensing module to sense proximity to said body tissue; and
   a single injector control module to control mixing of said varied dosages, and to activate said syringe driver module responsive to a user pressing a trigger and to signaling received from said vaccine quality detector and said contact sensing module.

2. The system according to claim 1 wherein said at least two needles are poultry vaccination needles.

3. The system according to claim 1 wherein said injector device is a single hand handheld device.

4. The system according to claim 1 wherein said electronic fluid delivery device is a portable device.

5. The system according to claim 1 further comprising an interconnecting cable for fluidly communicating said injector device and said fluid delivery device.

6. The system according to claim 5 wherein said cable is a flexible cable.

7. The system according to claim 5 wherein said cable comprises a fluid conductor for delivering variable vaccine dosages and said measured amount of said multiple vaccines of different types.

8. The system according to claim 5 wherein said cable comprises a power conductor for sharing electrical power between said injector device and said fluid delivery device.

9. The system according to claim 5 wherein said cable comprises a data communication conductor for communicating between said injector device and said fluid delivery device.

10. The system according to claim 1 wherein said injector device comprises a plurality of fluid mixing compartments for mixing said measured amount of said multiple vaccines of different types.

11. The system according to claim 10 wherein said injector device comprises a means to distribute said measured amount of said multiple vaccines of different types among said plurality of fluid mixing compartments.

12. The system according to claim 1 wherein said contact sensing module is a pressure sensor.

13. The system according to claim 1 wherein said electronic fluid delivery device includes one or more vaccine containers and at least one temperature storage module for controlling a temperature of said measured amount of said multiple vaccines of different types prior to injection.

14. The system according to claim 13 wherein said one or more vaccine containers are flexible bags.

15. The system according to claim 13 wherein said one or more vaccine containers are bottles.

16. The system according to claim 1 wherein said injector control module comprises motors to adjust a protrusion length for each of said at least two needles independently.

* * * * *